United States Patent [19]
Ni et al.

[11] Patent Number: 5,840,509
[45] Date of Patent: Nov. 24, 1998

[54] PROTEASE AND RELATED NUCLEIC ACID COMPOUNDS

[75] Inventors: Binhui Ni; Marc Paul; Xin Wu, all of Carmel, Ind.

[73] Assignee: Eli Lilly and Company, Indianapolis, Ind.

[21] Appl. No.: 890,542

[22] Filed: Jul. 9, 1997

Related U.S. Application Data

[60] Provisional application No. 60/022,049, Jul. 22, 1996.

[51] Int. Cl.$^6$ ............................. C12N 9/48; C12N 9/64; C12N 9/14; C12Q 1/37
[52] U.S. Cl. ........................... 435/23; 435/212; 435/219; 435/226
[58] Field of Search .............................. 435/23, 212, 219, 435/226; 424/852

[56] References Cited

PUBLICATIONS

Krajewska, M. et al. *Cancer Research* 57 (8);1605–1613 (1997).
Lazebnik, et al., *Nature*, 371, 346–347 (1994).
Nicholson et al., *Nature*, 376, 37–43 (1995).
D'Mello et al., *Proc. Natl. Acad Sci* USA, 90, 10989–10993, (1993).
Kuida et al., *Science*, 267, 2000–2003, (1995).
Cotman et al., *Molecular Neurobiology*, 10, 19–45 (1995).
Raff et al., *Science*, 262, 695–700, (1993).
Wood et al., *Neuron*, 11, 621–632, (1993).

*Primary Examiner*—Dian C. Jacobson
*Attorney, Agent, or Firm*—Paul J. Gaylo; David E. Boone

[57] ABSTRACT

The present invention provides for a novel ICE related protease and nucleic acids coding same. The present invention also provides a method to isolate an ICE related protease and related DNA compounds encoding this protease. The present invention further comprises a method using said protease to screen for inhibitors of apoptosis. Additionally, the invention further comprises a method of using said inhibitors of apoptosis in the treatment in human patients with the acquired disease states of brain ischemia, stroke, Alzheimer's disease, amyotrophic lateral sclerosis (ALS), head trauma, or other neurodegenerative disorders.

2 Claims, No Drawings

PROTEASE AND RELATED NUCLEIC ACID COMPOUNDS

This application claims the benefit of U.S. Provisional Application No. 06/022,049, filed Jul. 22, 1996.

FIELD OF THE INVENTION

The present invention relates to an isolated ICE related protease and related DNA compounds encoding this protease. The invention further relates to the use of the ICE related protease as a primer or probe for isolating additional proteases. The invention even further relates to the use of the ICE related protease to screen for inhibitors of ICE related proteases.

BACKGROUND OF THE INVENTION

The death of central neurons is widely recognized as a normal feature of vertebrate development. For example, during cerebellar development, granule neurons, which are among the most abundant neuronal phenotype, are generated postnatally in the external germinal layer where they differentiate, migrate to the granule layer and are finally innervated by mossy fiber axons. J. Altman, Postnatal Development Of The Cerebellar Cortex In The Rat, 3. Maturation Of The Components Of The Granule Layer, *J. Comp. Neurol.*, 145:465–513 (1972). More than 50% of these neurons die prior to completion of their postnatal migration. D. M. Landis, et al, Electron Microscopic Analysis Of Postnatal Histogenesis In The Cerebellar Cotex Of Staggerer Mutant Mice, *J. Comp. Neurol.*, 179:831–863 (1978). The precise nature of this fatal selection remains a mystery. Previous studies suggest that the death of these neurons occurs via apoptosis, a physiological mechanism by which a cell dies through activation of an intrinsic cell death or suicide program. M. C. Raff, et al, Programmed Cell Death And The Control Of Cell Survival: Lessons From The Nervous System, *Science*, 262:695–700 (1993) and K. A. Wood, et al, In Situ Labeling Of Granule Cells For Apoptosis-Associated DNA Fragmentation Reveals Different Mechanisms Of Cell Loss In Developing Cerebellum, *Neuron*, 11:621–632 (1993). Several lines of evidence suggest that apoptotic cell death is required for normal CNS development but is also involved in pathological neuronal death which occurs in neurodegenerative disorders such as Alzheimer's disease where neuronal cell loss is a prominent feature. C. W. Cotman, et al, A Potential Role For Apoptosis In Neurodegeneration And Alzheimer's Disease, *Mol. Neurobiol.*, 10:19–45 (1995); H. Lassmann, et al, Cell Death In Alzheimer's Disease Evaluated By DNA Fragmentation In Situ, Acta *Neuropathol.*, 89:35–41 (1995) and F. M. LaFerla, et al, The Alzheimer's AS Peptide Induces Neurodegeneration And Apoptotic Cell Death In Transgenic Mice, *Nature Genetics*, 9:21–29 (1995).

Several members of the ICE (interleukin-1β converting enzyme) family of proteases have recently been implicated in the intracellular cascade mediating the apoptotic death of various cell types. Although several ICE related proteases have been identified in cells from the immune system and various tumor cell lines, it is unknown whether any of these proteases are involved in neuronal apoptosis or how these proteases are activated. There is also evidence that ICE itself may not be the trigger for mammalian neuronal apoptosis because central neurons develop normally in ICE-deficient mice, despite major defects in ICE-dependent generation of mature interleukin-1 and other cytokines (P. Li et al., Mice Deficient in IL-1β Converting Enzyme Are Defective In Production of Mature IL-1β And Resistant To Endotoxic Shock, *Cell* 80:401–11 (1995) and K. Kuida et al., Altered Cytokine Export And apoptosis In Mice Deficient In Interleukin-1 Beta Converting Enzyme, *Science* 267:2000–3 (1995)). These findings strongly suggest that there are other cysteine protease(s) involved in neuronal apoptosis.

Understanding the cellular events underlying apoptosis may prove useful for developing neuroprotective strategies as well as therapeutic interventions for neurodegenerative disorders. Cultured cerebellar granule neurons have been characterized and utilized as a model to identify the intrinsic mechanisms underlying neuronal apoptosis. Postmitotic granule neurons can be readily maintained in vitro in their fully differentiated state for several weeks if depolarized with high concentrations of $K^+$. It has previously been shown that exposing cultured cerebellar granule neurons to nondepolarizing culture conditions (by lowering extracellular $[K^+]$) results in cell death accompanied by all the morphological and biochemical characteristics of apoptosis, including cytoplasmic blebbing, condensation/aggregation of nuclear chromatin and internucleosomal DNA fragmentation (G. Yan, et al., Depolarization Or Glutamate Receptor Activation Blocks Apoptotic Cell Death Of Cultured Cerebellar Granule Neurons, *Brain Res.* 656:43–51 (1994) and S. R. D'Mello, et al., Induction Of Apoptosis In Cerebellar Granul Neurons By Low Potassium: Inhibition By Insulin-like Growth Factor I And cAMP, *Proc. Natl. Acad. Sci. USA* 90:10989–93 (1993)). Cultured cerebellar granule neurons, therefore, represent a good model system for studying the cellular/molecular mechanisms underlying neuronal apoptosis.

A neuronal ICE related protease which affects apoptosis in neurons has now been identified. This ICE related protease was isolated from the rat CNS. A further understanding of the cellular events underlying apoptosis will prove useful for developing neuroprotective strategies as well as therapeutic interventions for neurodegenerative disorders.

SUMMARY OF THE INVENTION

The present invention provides an isolated amino acid compound which comprises the amino acid sequence SEQ ID NO:2 and functional equivalents thereof. Preferably, the amino acid compound is SEQ ID NO:2.

The invention also provides isolated nucleic acid compounds that comprise a nucleic acid sequence which encodes the presently provided amino acid compounds or parts thereof. Nucleic acid compounds which are DNA are preferred. The most preferred is the DNA compound SEQ ID NO:1.

Also provided by the present invention are nucleic acid vectors comprising nucleic acids which encode SEQ ID NO:2 or functional equivalents thereof. The preferred nucleic acid vectors are those which are DNA. The most preferred are those DNA vectors which comprise the DNA sequence which is SEQ ID NO:1.

The present invention also provides probes and primers useful for molecular biology techniques. A compound which encodes all or part of SEQ ID NO:1 and which is at least 18 consecutive base pairs in length is provided. Preferably, the 18 base pair or more compound is DNA.

DEFINITIONS

For purposes of clarity and as an aid in understanding the invention as disclosed and claimed herein, the following terms are defined hereinbelow. Terms and abbreviations which are not defined below are meant to have their normal meanings.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Part of SEQ ID NO:1" as used herein refers to at least 6 consecutive amino acid residues or more of SEQ ID NO:1.

The term "ICE related protease" as used herein refers to the amino acid sequence, SEQ ID NO:2. Other terms in the art referring to similar proteins are "apoptosin" or "caspase".

"mRNA" as used herein refer to RNA which has been transcribed either in vivo or in vitro, including, for example, RNA transcripts prepared in vitro via transcription of coding sequences of DNA by RNA polymerase.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter and other regulatory elements to control transcription of the inserted DNA.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells with polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by joining DNA molecules from different sources. The term "vector" as used herein includes Recombinant DNA cloning vectors and Recombinant DNA expression vectors.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid hybridization with another nucleic acid. (See the definition of "hybridization", supra.).

The following section provides a more detailed description of the present invention.

DETAILED DESCRIPTION OF THE INVENTION

The present invention provides an isolated amino acid compound having the amino acid sequence:

```
Met Asp Asn Asn Glu Thr Ser Val
 1               5

Asp Ser Lys Ser Ile Asn Asn Phe
                 10                   15

Glu Thr Lys Thr Ile His Gly Ser
             20

Lys Ser Met Asp Ser Gly Ile Tyr
                 25              30

Leu Asp Ser Ser Tyr Lys Met Asp
             35                40

Tyr Pro Glu Met Gly Leu Cys Ile
                             45

Ile Ile Asn Asn Lys Asn Phe His
     50                  55

Lys Ser Thr Gly Met Ser Ala Arg
                         60

Asn Gly Thr Asp Val Asp Ala Ala
 65                  70

Asn Leu Arg Glu Thr Phe Met Ala
                     75                  80

Leu Lys Tyr Glu Val Arg Asn Lys
             85

Asn Asp Leu Thr Arg Glu Glu Ile
                 90                       95
```

Column 5 (continued)

```
Met  Glu  Leu  Met  Asp  Ser  Val  Ser
               100
                    Lys  Glu  Asp  His  Ser  Lys  Arg  Ser
                    105                       110
Ser  Phe  Val  Cys  Val  Ile  Leu  Ser
          115                 120
               His  Gly  Asp  Glu  Gly  Val  Ile  Phe
                              125
Gly  Thr  Asn  Gly  Pro  Val  Asp  Leu
     130                      135
               Lys  Lys  Leu  Thr  Ser  Phe  Phe  Arg
                              140
Gly  Asp  Tyr  Cys  Arg  Ser  Leu  Thr
145                      150
               Gly  Lys  Pro  Lys  Leu  Phe  Ile  Ile
                              155                 160
Gln  Ala  Cys  Arg  Gly  Thr  Glu  Leu
                    165
               Asp  Cys  Gly  Ile  Glu  Thr  Asp  Ser
                    170                      175
Gly  Thr  Asp  Asp  Asp  Met  Ala  Cys
               180
               Gln  Lys  Ile  Pro  Val  Gly  Ala  Asp
               185                      190
Phe  Leu  Tyr  Ala  Tyr  Ser  Thr  Ala
          195                      200
```

Column 6 (continued)

```
Pro  Gly  Tyr  Tyr  Ser  Trp  Arg  Asn
               205
     Ser  Arg  Asp  Gly  Ser  Trp  Phe  Ile
          210                      215
               Gln  Ser  Leu  Cys  Ala  Met  Leu  Lys
                              220
     Leu  Tyr  Ala  His  Lys  Leu  Glu  Phe
     225                      230
               Met  His  Ile  Leu  Thr  Arg  Val  Asn
                              235                      240
     Arg  Lys  Val  Ala  Met  Glu  Phe  Glu
                         245
               Ser  Phe  Ser  Leu  Asp  Ala  Thr  Phe
                    250                      255
     His  Ala  Lys  Lys  Gln  Ile  Pro  Cys
                    260
               Ile  Val  Ser  Met  Leu  Thr  Lys  Glu
               265                      270
     Leu  Tyr  Phe  Tyr  His
               275
``` which is hereinafter designated SEQ ID NO:2.

Another embodiment of the present invention includes an isolated nucleic acid compound which comprises a nucleic acid compound which encodes for the amino acid compound provided. Particularly, this invention provides the isolated nucleic acid compound having the sequence:

```
GAATTCGGCT TGGTAGCGAC CGGCGCTCAG CTGGAATTCC GGGGAGCTTG GAACGGTACG     60

CGAAGAAAAG TGACC ATG GAC AAC AAC GAA ACC TCC GTG GAT TCA AAA TCC    111
                 Met Asp Asn Asn Glu Thr Ser Val Asp Ser Lys Ser
                  1               5                  10

ATT AAT AAT TTT GAA ACA AAG ACT ATC CAT GGA AGC AAG TCG ATG GAC    159
IlE Asn Asn Phe Glu Thr Lys Thr Ile His Gly Ser Lys Ser Met Asp
            15                  20                  25

TCT GGA ATA TAT CTG GAC AGC AGT TAC AAA ATG GAT TAC CCT GAA ATG    207
Ser Gly Ile Tyr Leu Asp Ser Ser Tyr Lys Met Asp Tyr Pro Gly Met
        30                  35                  40

GGC TTG TGT ATA ATA ATT AAT AAT AAG AAC TTC CAT AAA AGC ACT GGA    255
Gly Leu Cys Ile Ile Ile Asn Asn Lys Asn Phe His Lys Ser Thr Gly
 45                  50                  55                  60

ATG TCA GCT CGC AAT GGT ACC GAT GTC GAT GCA GCT AAC CTC AGA GAG    303
Met Ser Ala Arg Asn Gly Thr Asp Val Asp Ala Ala Asn Leu Arg Glu
                65                  70                  75

ACA TTC ATG GCC CTG AAA TAC GAA GTC AGG AAT AAA AAT GAC CTT ACT    351
Thr Phe Met Ala Leu Lys Tyr Glu Val Arg Asn Lys Asn Asp Leu Thr
            80                  85                  90

CGT GAA GAA ATT ATG GAA TTG ATG GAT AGT GTT TCT AAG GAA GAT CAC    399
Arg Glu Glu Ile Met Glu Leu Met Asp Ser Val Ser Lys Glu Asp His
        95                  100                 105

AGC AAA AGG AGC AGT TTT GTG TGT GTG ATT CTA AGT CAT GGA GAT GAA    447
Ser Lys Arg Ser Ser Phe Val Cys Val Ile Leu Ser His Gly Asp Glu
        110                 115                 120

GGA GTA ATT TTT GGA ACG AAC GGA CCT GTG GAC CTG AAA AAA CTA ACT    495
Gly Val Ile Phe Gly Thr Asn Gly Pro Val Asp Leu Lys Lys Leu Thr
125                 130                 135                 140

AGT TTC TTC AGA GGC GAC TAC TGC CGG AGT CTG ACT GGA AAG CCG AAA    543
Ser Phe Phe Arg Gly Asp Tyr Cys Arg Ser Leu Thr Gly Lys Pro Lys
            145                 150                 155
```

-continued

| | | | | | | | | | | | | | | | |
|---|---|---|---|---|---|---|---|---|---|---|---|---|---|---|---|
| CTC | TTC | ATC | ATT | CAG | GCC | TGC | CGA | GGT | ACA | GAG | CTG | GAC | TGC | GGT | ATT | 591
| Leu | Phe | Ile | Ile | Gln | Ala | Cys | Arg | Gly | Thr | Glu | Leu | Asp | Cys | Gly | Ile |
| | | | 160 | | | | | 165 | | | | | 170 | | |
| GAG | ACA | GAC | AGT | GGA | ACT | GAC | GAT | GAT | ATG | GCA | TGC | CAG | AAG | ATA | CCA | 639
| Glu | Thr | Asp | Ser | Gly | Thr | Asp | Asp | Asp | Met | Ala | Cys | Gln | Lys | Ile | Pro |
| | | 175 | | | | | 180 | | | | | 185 | | | |
| GTG | GGG | GCC | GAC | TTC | CTG | TAT | GCT | TAC | TCT | ACC | GCA | CCC | GGT | TAC | TAT | 687
| Val | Gly | Ala | Asp | Phe | Leu | Tyr | Ala | Tyr | Ser | Thr | Ala | Pro | Gly | Tyr | Tyr |
| | 190 | | | | | 195 | | | | | 200 | | | | |
| TCC | TGG | AGA | AAT | TCA | AGG | GAC | GGG | TCA | TGG | TTC | ATC | CAG | TCA | CTT | TGC | 735
| Ser | Trp | Arg | Asn | Ser | Arg | Asp | Gly | Ser | Trp | Phe | Ile | Gln | Ser | Leu | Cys |
| 205 | | | | | 210 | | | | | 215 | | | | | 220 |
| GCC | ATG | CTG | AAA | CTG | TAC | GCG | CAC | AAG | CTG | GAA | TTC | ATG | CAC | ATC | CTC | 783
| Ala | Met | Leu | Lys | Leu | Tyr | Ala | His | Lys | Leu | Glu | Phe | Met | His | Ile | Leu |
| | | | | 225 | | | | | 230 | | | | | 235 | |
| ACT | CGT | GTT | AAC | CGG | AAG | GTG | GCC | ATG | GAA | TTT | GAG | TCC | TTC | TCC | CTG | 831
| Thr | Arg | Val | Asn | Arg | Lys | Val | Ala | Met | Glu | Phe | Glu | Ser | Phe | Ser | Leu |
| | | | 240 | | | | | 245 | | | | | 250 | | |
| GAC | GCC | ACT | TTC | CAC | GCA | AAG | AAA | CAG | ATC | CCG | TGT | ATT | GTG | TCA | ATG | 879
| Asp | Ala | Thr | Phe | His | Ala | Lys | Lys | Gln | Ile | Pro | Cys | Ile | Val | Ser | Met |
| | | 255 | | | | | 260 | | | | | 265 | | | |
| CTC | ACA | AAA | GAA | CTG | TAC | TTT | TAT | CAC | TAAAGGAATG | ACTGGGAGTG | | | | | | 926
| Leu | Thr | Lys | Glu | Leu | Tyr | Phe | Tyr | His | | | | | | | |
| | 270 | | | | | 275 | | | | | | | | | |

GGGTAGGGGC ATGTTTCTGT TTTGGTTTTT TTTTGGTTTT TGGTTTGTTT TTTTTTTTTT        986

TATTTGAATG CCAAATGAGA AAACTGTCAG GGAGACTTTT TTTTTCCCCT CTCATTTAAA       1046

TCAAATCCGA TGTTCCAGGT CGTCATTGAA CAATACCACT GCCTGCAATG CAGCCACAAT       1106

ACAATACCTC AGCTTTGATA TCAGCCGGAA TTCCGCCGAT ACTGACGGGC TCCAGGAGTC       1166

AAGCCGAATT C                                                           1177 which is hereinafter designated as SEQ ID NO:1. Preferably, the nucleic acid is a compound encompassing nucleotides 76 through 906 of SEQ ID NO: 1.

The present invention provides a nucleic acid which encodes the protein SEQ ID NO:2, an ICE related protease designated as ICE related protease, was isolated from the rat central nervous system. ICE related protease is present in the CNS and is enriched in central neurons including pyramidal neurons and granule neurons of the hippocampus and cerebral cortex. Data suggests that overexpression of ICE related protease could be involved in a neuronal death cascade in mammalian neurons. A further understanding of the cellular events underlying apoptosis will prove useful for developing neuroprotective strategies as well as therapeutic interventions for head traumas, ALS, Alzheimer's, stroke, brain ischemia, as well as a variety of other neurodegenerative disorders involving apoptosis.

The present invention may be used to assay for a substance that inhibits apoptosis thereby effecting neuronal death cascade in cells. Accordingly, it is possible to use the above identified method to identify substances which may be useful in the treatment of Alzheimer's, stroke, brain ischemia, head traumas, ALS and other neurodegenerative disorders.

Determination of whether a cDNA isolated has the biological activity of ICE related protease can be accomplished by expressing the cDNA in a mammalian cell line, by standard techniques, and assessing whether expression in the cell of the protein encoded by the cDNA causes cell death.

Skilled artisans will recognize that the protease of the present invention can be isolated from rat central nervous system tissue or synthesized by a number of different methods. The amino acid compounds of the invention can be made by chemical methods well known in the art, including, for example, solid phase peptide synthesis, or recombinant methods. Both methods are described in U.S. Pat. No. 4,617,149, incorporated herein by reference. The principles of solid phase chemical synthesis of polypeptides are well known in the art and may be found in general texts in the area. See, e.g., H. Dugas and C. Penney, BIOORGANIC CHEMISTRY, (1981) Springer-Verlag, N.Y., pgs. 54–92.

The proteins of the present invention may also be produced by recombinant methods. Recombinant methods are preferred if a high yield is desired. A general method for the construction of any desired DNA sequence is provided in J. Brown, et al., Methods in Enzymology, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes can be used for cloning of DNA sequences in constructing the vectors of this invention.

Prokaryotes may also be employed in the production of the protein of interest. For example, the *Escherichia coli* K12 strain 294 (ATCC No. 31446) is useful for the prokaryotic expression of foreign proteins. Other strains of *E. coli* which may be used (and their relevant genotypes) include the following.

Strain Genotype

DH5a F⁻(Æ80dlacZΔM15), Δ(1acZgA-arg F)U169 SupE44, 1⁻, hsdR17($r_k$-,$m_k$+), recA1, endA1, gyrA96, thi-1, relA1

HB101 supE44, hsdS20($r_B^-$ $m_B^-$), recA13, ara-14, proA2 lacY1, galK2, rpsL20, xyl-5, mtl-1, mcrB, mrr JM109 recA1, e14⁻(mcrA), supE44, endA1, hsdR17($r_K^-$, $m_K^+$), gyrA96, relA1, thi-1, Δ(lac-proAB), F'[traD36, proAB+ lacI$^q$,lacZΔM15]

RR1 supE44, hsdS20($r_B^-$ $m_B^-$), ara-14 proA2, lacY1, galK2, rpsL20, xyl-5, mtl-5 c1776 F⁻, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, 1⁻

294 endA, thi⁻, hsr⁻, hsm$_k^+$ (U.S. Pat. No. 4,366,246)

LE392 F⁻, hsdR514 (r⁻m⁻), supE44, supF58, lacY1, or Dlac(I-Y)6, galK2, glaT22, metB1, trpR55, 1⁻

XL1 Blue recA1, endA1, gyrA96, thi, hsdR17($r_k$,$m_k$+), supE44, relA1, 1⁻, Δ(lac), [F', proAB, lacIqZΔM15, Tn10(tet$^R$)]

These strains, as well as other strains, are commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra.

Promoters suitable for use with prokaryotic hosts include the β-lactamase [vector pGX2907 (ATCC 39344) contains the replicon and β-lactamase gene] and 20 lactose promoter systems [Chang et al., Nature (London), 275:615 (1978); and Goeddel et al., Nature (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolated from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting, and are not meant to limit the invention in any way.

The proteins of this invention may also be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. A variety of eukaryotic host cells are available from depositories such as the American Type Culture Collection (ATCC) and are suitable for use with the vectors of the present invention. The choice of a particular host cell depends to some extent on the particular expression vector used.

Host cells suitable for use in the present invention include but are not limited to:

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| AV12-664 | Syrian Hamster | ATCC CRL 9595 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embyronal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |
| CHO-K1 | Chinese Hamster Ovary | ATCC CCL 61 |

A preferred eukaryotic host cell line employed in this invention is the widely available cell line HeLa. As noted above, this cell line is available from the American Type Culture Collection under the accession number ATCC CCL 2. The HeLa cell line was constructed from a human adenocarcinoma of the cervix.

A wide variety of vectors, some of which are discussed below, exists for the transformation of such mammalian host cells, but the specific vectors described herein are in no way intended to limit the scope of the present invention. The sequences encoding the illustrative proteins of the present invention can be easily inserted in any of the vectors described herein through routine purification, ligation and transfection techniques.

Some illustrative vectors include the pSV2-type vectors which comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, Cell, 35:705–713 (1984).

Plasmids constructed for expression of the proteases of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken oval-bumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., Proceedings of the National Academy of Sciences (USA), 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

Another useful expression vector system employs one of a series of vectors containing the BK enhancer, an enhancer derived from the BK virus, a human papovavirus. Other useful vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

An additional eucaryotic expression vector is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, all of which are herein incorporated by reference. Escherichia coli K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

The preferred eucaryotic expression vector employed in the present invention is pcDNA3, a commercially available high level expression vector from Invitrogen which has an expanded multiple cloning site to facilitate cloning of inserts. The vector pcDNA3 contains an enhancer-promoter sequence of human cytomeglovirus, a SV40 origin, an f1 origin, an ampicillin resistance gene, a neomycin resistance gene and polyadenylation signal and transcription termination sequence for bovine growth hormone. pcDNA3 functions when introduced into a variety of host cells as described herein. The preferred host cells for pcDNA3 are HeLa cells.

Transfection of the mammalian cells can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmids discussed above, it is well known in the art that some viruses are also appropriate vectors. For example, the adenovirus, the adeno-associated virus, the vaccinia virus, the herpes virus, the baculovirus, and the Rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus Saccharomyces cerevisiae, or common baker's yeast, is the most commonly used eukaryotic microorganism, although a number of other strains are commonly available. For expression in Saccharomyces sp., the plasmid YRp7 (ATCC-40053), for example, is commonly used. See, e.g., L. Stinchcomb, et al., Nature (London), 282:39 (1979); J. Kingsman et al., Gene, 7:141 (1979); S. Tschemper et al., Gene, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of Zymomonas mobilis (U.S. Pat. No. 5,000,000 issued Mar. 19, 1991, incorporated herein by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec—hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:1 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the proteins of SEQ ID NO:1 are shown below:

| Original Residue | Exemplary Substitutions |
|---|---|
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:1 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The genes encoding the molecules of the present invention may be produced using synthetic methodology. This synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the fusion proteins are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See, e.g., M. J. Gait, ed., OLIGONUCLEOTIDE SYNTHESIS, A PRACTICAL APPROACH, (1984).

The synthetic gene may be designed to possess restriction endonuclease cleavage sites at either end of the transcript to facilitate isolation from and integration into expression and amplification plasmids. The choice of restriction sites are chosen so as to properly orient the coding sequence with control sequences to achieve proper in-frame reading and expression of the molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818.

In addition to the deoxyribonucleic acid of SEQ ID NO:1, this invention also provides ribonucleic acids (RNA) which comprise the RNA sequence:

| | | | | | |
|---|---|---|---|---|---|
| GAAUUCGGCU | UGGUAGCGAC | CGGCGCUCAG | CUGGAAUUCC | GGGGAGCUUG | GAACGGUACG | 60 |
| CGAAGAAAAG | UGACCAUGGA | CAACAACGAA | ACCUCCGUGG | AUUCAAAAUC | CAUUAAUAAU | 120 |
| UUUGAAACAA | AGACUAUCCA | UGGAAGCAAG | UCGAUGGACU | CUGGAAUAUA | UCUGGACAGC | 180 |
| AGUUACAAAA | UGGAUUACCC | UGAAAUGGGC | UUGUGUAUAA | UAAUUAAUAA | UAAGAACUUC | 240 |
| CAUAAAAGCA | CUGGAAUGUC | AGCUCGCAAU | GGUACCGAUG | UCGAUGCAGC | UAACCUCAGA | 300 |
| GAGACAUUCA | UGGCCCUGAA | AUACGAAGUC | AGGAAUAAAA | AUGACCUUAC | UCGUGAAGAA | 360 |
| AUUAUGGAAU | UGAUGGAUAG | UGUUUCUAAG | GAAGAUCACA | GCAAAAGGAG | CAGUUUUGUG | 420 |
| UGUGUGAUUC | UAAGUCAUGG | AGAUGAAGGA | GUAAUUUUUG | GAACGAACGG | ACCUGUGGAC | 480 |
| CUGAAAAAAC | UAACUAGUUU | CUUCAGAGGC | GACUACUGCC | GGAGUCUGAC | UGGAAAGCCG | 540 |
| AAACUCUUCA | UCAUUCAGGC | CUGCCGAGGU | ACAGAGCUGG | ACUGCGGUAU | UGAGACAGAC | 600 |
| AGUGGAACUG | ACGAUGAUAU | GGCAUGCCAG | AAGAUACCAG | UGGGGGCCGA | CUUCCUGUAU | 660 |
| GCUACUCUA | CCGCACCCGG | UUACUAUUCC | UGGAGAAAUU | CAAGGGACGG | GUCAUGGUUC | 720 |
| AUCCAGUCAC | UUUGCGCCAU | GCUGAAACUG | UACGCGCACA | AGCUGGAAUU | CAUGCACAUC | 780 |
| CUCACUCGUG | UUAACCGGAA | GGUGGCCAUG | GAAUUUGAGU | CCUUCUCCCU | GGACGCCACU | 840 |
| UUCCACGCAA | AGAAACAGAU | CCCGUGUAUU | GUGUCAAUGC | UCACAAAAGA | ACUGUACUUU | 900 |
| UAUCACUAAA | GGAAUGACUG | GGAGUGGGGU | AGGGGCAUGU | UUCUGUUUUG | GUUUUUUUUU | 960 |
| GGUUUUUGGU | UUGUUUUUUU | UUUUUUUAUU | UGAAUGCCAA | AUGAGAAAAC | UGUCAGGGAG | 1020 |
| ACUUUUUUUU | UCCCCUCUCA | UUUAAAUCAA | AUCCGAUGUU | CCAGGUCGUC | AUUGAACAAU | 1080 |
| ACCACUGCCU | GCAAUGCAGC | CACAAUACAA | UACCUCAGCU | UUGAUAUCAG | CCGGAAUUCC | 1140 |
| GCCGAUACUG | ACGGGCUCCA | GGAGUCAAGC | CGAAUUC | | | 1177 | hereinafter referred to as SEQ ID NO: 3, or the complementary ribonucleic acid, or a fragment of either SEQ ID NO: 3 or the complement thereof. Preferably, the ribonucleic acid is a compound encompassing nucleotides 76 through 906 of SEQ ID NO: 3. The ribonucleic acids of the present invention may be prepared using the polynucleotide synthetic methods discussed supra or they may be prepared enzymatically using RNA polymerases to transcribe a DNA template.

Preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al. ,supra, at 18.82–18.84.

This invention also provides nucleic acids, RNA or DNA, which are complementary to SEQ ID NO:1, nucleotides 76 through 906 of SEQ ID NO: 1, SEQ ID NO: 3, or nucleotides 76 through 906 of SEQ ID NO: 3.

The present invention also provides probes and primers useful for molecular biology techniques. A compound which encodes for SEQ ID NO:1, nucleotides 76 through 906 of SEQ ID NO: 1, SEQ ID NO: 3, nucleotides 76 through 906 of SEQ ID NO: 3, or a complementary sequence of SEQ ID NO: 1, nucleotides 76 through 906 of SEQ ID NO: 1, SEQ ID NO: 3, nucleotides 76 through 906 of SEQ ID NO: 3, or a fragment thereof, and which at least 18 base pairs in length, and which will selectively hybridize to rat genomic DNA or messenger DNA encoding ICE related protease, is provided. Preferably, the 18 or more base pair compound is DNA.

Primers and probes may be obtained by means well known in the art. For example, once an ICE related protease is isolated, restriction enzymes and subsequent gel separation may be used to isolate the fragment of choice.

The term "selectively hybridize" as used herein may refer to either of two situations. In the first such embodiment of this invention, the nucleic acid compounds described supra hybridize to rat ICE related protease under more stringent hybridization conditions than these same nucleic acid compounds would hybridize to an analogous ICE related protease of another species. In the second such embodiment of this invention, these probes hybridize to the ICE related protease under more stringent hybridization conditions than other related compounds, including nucleic acid sequences encoding other ICE related proteases.

These probes and primers can be prepared enzymatically as described supra. In a most preferred embodiment these probes and primers are synthesized using chemical means as described supra.

Those skilled in the art will recognize the techniques associated with probes and primers are well known. For example, all or part of the probes or primers may be used to hybridize to the coding sequence. Then, through PCR amplification, the full length sequence may be generated. The full length sequence can be subsequently subcloned into any vector of choice. Alternatively, the primers or probes may be radioactively labeled at the 5' end in order to screen cDNA libraries by conventional means. A primer or probe can be labeled with a radioactive element which provides for an adequate signal as a means for detection and has sufficient half-life to be useful for detection, such as $^{32}$p, $^{3}$H, $^{14}$C or the like. Other materials which can be used to label the primer or probe include antigens that are recognized by a specific labeled antibody, fluorescent compounds, enzymes, antibodies specific for a labeled antigen, and chemiluminescent compounds. An appropriate label can be selected having regard to the rate of hybridization and binding of the primer or probe to the nucleotide to be detected and the amount of nucleotide available for hybridization.

Recombinant DNA cloning vectors and expression vectors comprising the nucleic acids of the present invention can also be prepared. Many such vectors are described above. The preferred nucleic acid vectors are those which are DNA. The preferred recombinant DNA vectors comprise the isolated DNA sequence SEQ ID NO:1. The most preferred recombinant DNA vectors comprise nucleotides 76 through 906 of SEQ ID NO:1.

The skilled artisan understands that the type of cloning vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of the nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The plasmid of the present invention can be readily modified to construct expression vectors in a variety of organisms, including, but not limited to, E. coli, Sf9 (as host for baculovirus), Spodoptera and Saccharomyces.

One of the most widely employed techniques for altering a nucleic acid sequence is by way of oligonucleotide-directed site-specific mutagenesis. B Comack, "Current Protocols in Molecular Biology", 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly useful are plasmids which contain regions such as the f1 intergenic region. This region allows the generation of single-stranded templates when a helper phage is added to the culture harboring the "phagemid".

After the annealing of the oligonucleotide, to the template, a DNA-dependent DNA polymerase is then used to synthesize the second strand from the oligonucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for E. coli can be followed to construct analogous vectors for other organisms, merely by substituting, if necessary, the appropriate regulatory elements using techniques well know to skilled artisans.

Host cells which harbor the nucleic acids provided by the present invention can also be prepared. One suitable host cell is an Xenopus sp. oocyte which has been injected with RNA or DNA compounds of the present invention. Most preferred oocytes of the present invention are those which harbor a sense mRNA of the present invention. Other preferred host cells include HeLa and E.coli cells which have been transfected and/or transformed with a vector which comprises a nucleic acid of the present invention.

A method for constructing a recombinant host cell capable of expressing SEQ ID NO:2 is also possible with regard to the present invention, said method comprising transforming a host cell with a recombinant DNA vector that comprises an isolated DNA sequence which encodes SEQ ID NO:2. The preferred host cell is HeLa cells. A preferred vector for expression is one which comprises SEQ ID NO:1, more preferably nucleotides 76–906 of SEQ ID NO:1. Another preferred host cell for this method is E.coli. Transformed host cells may be cultured under conditions well known to skilled artisans such that SEQ ID NO: 2 is expressed, thereby producing the sequence of ICE related protease in the recombinant host cell.

In developing agents which inhibit ICE related protease, it would be desirable, therefore, to determine those agents which bind an ICE related protease, most preferably a protease corresponding to the amino acid sequence of SEQ ID NO:2. Generally, such an assay includes a method for determining whether a substance is a functional ligand of ICE related protease, said method comprising contacting a functional compound of ICE related protease with said substance, monitoring binding activity by physically detectable means, and identifying those substances which effect a chosen response. Preferably, the physically detectable means is binding of ligand in an oocyte transient expression system.

The ability of the ICE related protease to cleave the appropriate substrate is essential in the development of a multitude of indications. The development of agents which interfere or inhibit this cleavage is, therefore, important in the development of therapeutic agents effective in the treatment of neurodegenerative conditions.

As used herein, the term "ICE related protease substrate" refers to any peptide or protein, whether naturally produced, recombinantly produced, or chemically synthesized, which can be hydrolyzed by an ICE related protease, be it the full length ICE related protease, whether derived by isolation or purification from a biological source or by expression of a cloned gene encoding ICE related protease or its analogs, and fragments of any such protein, including fragments obtained by digestion of the protein or a portion thereof, fragments obtained by expression of a gene coding for a portion of the protein, and synthetic peptides having amino acid sequences corresponding to a portion of the protein.

ICE related protease substrates for the assays of the present invention can be provided as a test reagent in a variety of forms. ICE related protease can be obtained by biochemical isolation or purification from natural sources or by expression of recombinant DNA clones encoding the protein or a functional protein thereof.

Some fragments of the substrate will comprise a sequence of amino acids sufficient for recognition and cleavage by the proteases of the present invention. Isolation of the substrate protein from biological material usually will involve purification by conventional techniques such as chromatography, particularly affinity chromatography. Purified protein or fragments thereof can be used to prepare monoclonal antibodies or polyclonal antibodies which can then be used in affinity purification according to conventional procedures.

Such an inhibition assay includes a method for determining whether a protein sequence is a functional substrate of the ICE related protease of the instant invention, said method comprising contacting a functional ICE related protease of the instant invention with said protein sequence, monitoring proteolysis activity by physically detectable means, and then identifying those substances which effect a chosen response.

A variety of convenient methods are applicable to the detection of proteolytic cleavage of the protein substrate in the presence of a test sample. Several of the presently more preferred methods are described below, however, it will be recognized by the skilled worker in the field that many other methods can be applied to this step without departing from the inventive features thereof. In general, any method can be used for this purpose which is capable of detecting the occurrence of proteolytic cleavage of the ICE related protease protein substrate. Such can be afforded by appropriate design of the protein substrate such that cleavage produces a signal producing species, e.g., an optically responsive product such as a colored or fluorescent dye.

Another principal approach involves the sensitive detection of one or more cleavage products such as by immunoassay. Any fragment which appears upon incubation with the proteases of the present invention can be the object of detection.

The detection of one or more cleavage products characteristic of the pathologic proteolytic activity can be accomplished in many ways. One such method involves the procedure commonly known as the Western blot. Typically, after incubation of ICE related protease with a protease of the present invention, gel electrophoresis is performed to separate the components resulting in the reaction mixture. The separated protein components are then transferred to a solid matrix such as a nitrocellulose or nylon membrane.

An antibody specific to a fragment characteristic of protein degradation is then reacted with the components fixed to the membrane and detected by addition of a secondary enzyme-labeled antibody conjugate. The location of the resulting bound conjugate is developed with a chromogenic substrate for the enzyme label.

A variety of immunoassay formats which are amenable to currently available test systems can also be applied to the detection of protein fragments. Typically, the ICE related protease substrate will be incubated with a ICE related protease of the present invention. The resulting intact ICE related protease is then rendered immobilized (such as by capture onto a solid phase), or alternatively, the protein protease is incubated with an immobilized form of the protein substrate. Proteolytic cleavage is then detected by reacting the immobilized protein substrate with an antibody reagent directed to a portion of the protein substrate which is cleaved from the protein substrate, or which defines the cleavage site.

Capture or immobilization of the protein substrate can be accomplished in many ways. An antibody can be generated specific to an epitope of protein which is not on the cleavable fragment. Such an antibody can be immobilized and used to capture or immobilize intact protein. Alternatively, a ligand or hapten can be covalently attached to protein and a corresponding immobilized receptor or antibody can be used to capture or immobilize protein. A typical ligand/receptor pair useful for this purpose is biotin/avidin. Examples of haptens useful for this purpose are fluorescein and digitoxigenin.

The solid phase on which protein substrate is immobilized or captured can be composed of a variety of materials including microtiter plate wells, test tubes, strips, beads, particles, and the like. A particularly useful solid phase is magnetic or paramagnetic particles. Such particles can be derivatized to contain chemically active groups that can be coupled to a variety of compounds by simple chemical reactions. The particles can be cleared from suspension by bringing a magnet close to a vessel containing the particles. Thus, the particles can be washed repeatedly without cumbersome entrifugation or filtration, providing the basis for fully automating the assay procedure.

Labels for the primary or secondary antibody reagent can be selected from those well known in the art. Some such labels are fluorescent or chemiluminescent labels, radioisotopes, and more preferably, enzymes for this purpose are alkaline phosphatase, peroxidase, and β-galactosidase. These enzymes are stable under a variety of conditions, have a high catalytic turnover rate, and can be detected using simple chromogenic substrates.

Proteolytic cleavage of the protein substrate can also be detected by chromatographic techniques which will separate and then detect the protein fragments. High performance liquid chromatography is particularly useful in this regard. In applying this technique, a fluorescently tagged protein is prepared. After incubation with the protease of the present invention, the reaction mixture is applied to the chromatographic column and the differential rate of migration of fluorescent fragments versus intact protein is observed.

The instant invention provides such a screening system useful for discovering agents which inhibit the cleavage of the ICE related protease substrate of the instant invention, said screening system comprising the steps of:

a) isolating a ICE related protease;

b) exposing said ICE related protease to a potential inhibitor of this protease;

c) introducing a suitable substrate; and d) quantifying the amount of cleavage of the substrate, relative to a control in which no potential inhibitor has been added.

This allows one to rapidly screen for inhibitors of the protein protease of the instant invention. Utilization of the screening system described above provides a sensitive and rapid means to determine compounds which inhibit the proteases of the instant invention. This screening system may also be adapted to automated procedures such as a Pandex® (Baxter-Dade Diagnostics) system allowing for efficient high-volume screening of potential therapeutic agents.

In such a screening protocol a protein protease is prepared as elsewhere described herein, preferably using recombinant DNA technology. A sample of a test compound is then introduced to the reaction vessel containing the protein protease followed by the addition of an appropriate substrate. In the alternative the substrate may be added simultaneously with the test compound.

A bioactivity assay system which determines the response of ICE related protease to a compound is clear. The instant invention provides such a bioactivity assay, said assay comprising the steps of:

a) transfecting a mammalian host cell with an expression vector comprising DNA encoding ICE related protease;

b) culturing said host cell under conditions such that the ICE related protease protein is express;

c) exposing said host cell so transfected to a test compound; and d) measuring the change in a physiological condition known to be influenced by the presence of ICE related protease relative to a control in which the transfected host cell is not exposed to a test compound.

The present invention comprises a method of using said inhibitors of ICE related protease in the treatment in human patients with the acquired disease states of brain ischemia, stroke, Alzheimer's disease, amyotrophic lateral sclerosis (ALS), head trauma, or other neurodegenerative disorders.

The proteins of this invention as well as fragments of these proteins may be used as antigens for the synthesis of antibodies The term "antibody" as used herein describes antibodies, fragments of antibodies (such as, but not limited, to Fab, Fab', $Fab_2$, and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See, e.g. , C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in a response to a specific antigenic site, or epitope, recognized on the immunogenic substance.

Chimeric antibodies are described in the U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28,1989 to M. Boss, et al, the entire contents of which are herein incorporated by reference. The Boss patent teaches the simultaneous co-expression of the heavy and light chains of the antibody in the same host cell.

The approach of U.S. Pat. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See, e.g. R. E. Bird, et al., *Science* 242:423–426 (1988); PCT Publication No. WO 88/01649, which was published 10 Mar. 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vitro administration to mammals, of the antibodies of the present invention.

The following examples intended to further illustrate the present invention and are not to be interpreted as limiting on the scope thereof. While the examples and detailed description sections of the present invention are sufficient to guide anyone of ordinary skill in the art in the practice of the present invention, skilled artisans are also directed to *Molecular Cloning A Laboratory Manual* Second Edition, Sambrook,J., Fritsch, E. F., and Maniatis, T., Cold Spring Harbor Press 1989 and *Current Protocols In Molecular Biology*, Ausubel, F. M., Brent,R., Kingston,R. E., Moore, D. D., Seidman,J. G., Smith, J. A., and Struhl, K.,Ed. Greene Publishing Associates and Wiley-Interscience 1989. The aforementioned resources provide an excellent technical supplement to any discourse in genetic engineering.

EXAMPLES

EXAMPLE 1. FORMULATIONS

The compounds which are inhibitors of said ICE related protease are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, the compounds which are inhibitors of said ICE related protease associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates,, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid compositions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, acetyl alcohol, and cellulose acetate.

The liquid forms in which the novel compositions of the present invention may be incorporated for administration orally injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compositions may be administered, preferably orally or nasally, from devices which deliver the formulation in an appropriate manner.

The following examples illustrate the pharmaceutical compositions of the present invention.

Formulation Preparation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient | 250.0 mg |
| Isotonic saline | 1000 ml |

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

EXAMPLE 2

CLONING OF AN ICE RELATED PROTEASE FROM CNS 2A. Library screening and cloning of the ICE related protease In order to clone the ICE related protease of the present invention, a rat brain cDNA library obtained from Stratagene, Inc. (LaJolla, Calif. Catalog #936501) was screened using low stringency conditions. Approximately, $5 \times 10^5$ plaques were screened using filter hybridization. For screening, 21mer oligonucleotides derived from the consensus sequence of ICE related proteases, including ICE, CED-3 and CPP32/YAMA/apopain, were radioactively labeled with $^{32}$P-r-ATP. Hybridization was performed overnight at 42° C. in 50% formamide, 5×SSPE (0.75M NaCl, 50 mM $NaH_2PO_4.H_2O$, pH 7.4, 5 mM EDTA), 5×Denhardt solution (1.0 g Ficoll, 1.0 g Polyvinyl pyrrolidone, 1.0 g BSA Pentax Fraction V per liter of water), 0.1% SDS, and 100 µg/ml denatured salmon sperm DNA. The buffer was carefully discarded and the filters were washed in 2×SSC containing 0.3M NaCl, 0.03M sodium citrate, pH 7.0 and 0.5% SDS at room temperature for 30 min. followed by an additional wash in 2×SSC and 0.1 % SDS at 55° C. for 30 min. The filters were dried by blotting on Whatman 3M paper at room temperature and then autoradiographed using an intensifying screen to enhance the signal. After developing, the film was aligned with the filters to select positive plaques. Five positive clones which strongly hybridized to the $^{32}$P-labeled probe were isolated. Two clones were further confirmed by rehybridization of their excised plasmids with the labeled ICE related protease probe. One of the clones, designated ICE related protease, was then sequenced in both directions and analyzed using GCG programs (University of Wisconsin) as described in B. Ni, et al., Cloning And Expression Of A cDNA Encoding A Brain-specific $Na^+$-dependent Inorganic Phosphate Cotransporter, *Proc. Natl. Acad. Sci. USA* 91:5607–11 (1994). A commercially available software package was utilized for sequence comparisons.

2B. DNA Sequencing And Sequence Analysis

The nucleotide sequence of the ICE related protease cDNA clone was determined for both strands. Sequence reactions were done using double-stranded DNA templates, sequence-specific oligonucleotide primers, fluorescently labeled dideoxynucleotide terminators(Applied Biosystems) and Ampli-Taq polymerase in cycle-sequencing reactions modified as described (B. Ni, et al., Cloning And Expression Of A cDNA Encoding A Brain-specific $Na^+$-dependent Inorganic Phosphate Cotransporter, *Proc. Natl. Acad. Sci. USA* 91:5607–11 (1994). Individual sequences were assembled with an Applied Biosystems model 670 Inherit sequence analysis system and edited with commercially available software. Sequences were manipulated and analyzed with programs from the Genetics Computer Group. Sequences were compared with sequence data bases by using an available software package at the National Center for Biotechnology Information.

Sequence analysis of ICE related protease predicted an open reading frame of 831 bases, corresponding to a protein of 277 amino acids with an apparent molecular mass of 31,449 Da (32 kDa). The ATG initiation codon at position 1, which is preceded by an upstream in-frame stop codon, matches the Kozak consensus initiation sequence (CCATGG) for the initiation of translation (M. Kozak, Compilation And Analysis Of Sequences Upstream From The Translation Start Site In Eukaryotic mRNAs, *Nucleic Acid Res.* 12:857–72 (1984)). A computer analysis revealed that the protein encoded by the ICE related protease-1 shares sequence similarity at the amino acid level with those of ICE related proteases such as Nedd2 and CPP32/YAMA/apopain which have recently been cloned from tumor cell lines (T. Fernandes-Alnemri, et al., CPP32, A Novel Human Apoptotic Protein With Homology To Caenorhabditis Elegans Cell Death Protein Ced-3 And Mammalian Interlukin-1b-converting Enzyme, *J. Biol. Chem*, 269:30761–64 (1995) and D. W. Nicholson, et al., Identification And Inhibition Of The ICE/CED-3 Protease Necessory For Mammalian Apoptosis, *Nature*, 376:37–43 (1995); and M. Tewari, et al., Yama/CPP32β, A Mammalian Homolog Of CED-3, Is A CrmA-inhibitable Protease That Cleaves The Death Substrate Poly-ribose Polymerase, *Cell* 8:801–9 (1995)).

Expression of the ICE related protease gene in multiple tissues was examined by probing polyA$^+$ RNA from heart, brain, lung, liver, skeletal muscle, kidney and testis. The ICE related protease probe detected a single mRNA species of 2.8 kb in size in heart, brain, lung, liver and muscle but not in the kidney or testis fractions.

2C. DNA transfection and soluble DNA isolation

To confirm that ICE related protease encodes a cysteine protease responsible for apoptosis, ICE related protease and CPP32/YAMA/apopain cDNAs were respectively subcloned into the mammalian expression vector, pcDNA3, which contains the human cytomegalovirus (CMV) promoter pcDNA3 is commercially available from Invitrogen (Catalog #V790-20). The resulting expression vectors, pcDNA3-ICE related protease and pcDNA3-CPP32, were then introduced into eucaryotic host cells. The host cells, HeLa cells, were routinely maintained at 37° C. in Dulbecco's modified Eagle's medium (DMEM) with 10% fetal bovine serum (FCS), 100 units/ml of penicillin, and 100 μg/ml of streptomycin under 5% $CO_2$/95% air. DNA transfection was carried out using the LIPOFECTAMINE™ (Catalog #18324-012, BRL, Bethesda Res. Lab., Bethesda, Md.) method as described by the manufacturer. Briefly, prior to transfection, the culture medium was changed to OPTI-MEM™ (Commercially available from BRL, Bethesda, Md., Catalog #31985). LIPOFECTAMINE and 16 μg of pure DNA (pcDNA3-ICE related protease or vector only) were added to $5×10^5–10^6$ cells cultured in a 10 cm dish in 8 ml of OPTI-MEM medium. The cells were cultured at 37° C. for 5 hr followed by addition of 10% FCS to stop the transfection. The transfected cells were cultured for 48 hr before harvesting DNA for fragmentation analysis. The cells were harvested and washed with PBS buffered saline. Cell pellets were lysed with 100 μl of lysis buffer (1% NP-40, 20 mM EDTA, and 50 mM Tris-HCl, pH 7.5) and centrifuged for 5 min at 5,000×g. The supernatants were collected and the pellets were extracted with the same amount of lysis buffer. The supernatants were treated with RNase A (final concentration 5 μg/μl) for 2 h at 37° C. and then with proteinase K (final concentration 2.5 μg/μl) overnight at 56° C. The DNA was precipitated after addition of 1/10 (v/v) of 3M KAc and 1 vol. of isopropyl alcohol for 1 h at 4° C. The DNA was dissolved in loading buffer and separated on a 1.5% agarose gel. Soluble DNA isolated from transiently transfected pcDNA3-ICE related protease and pcDNA3-CPP32 revealed strong nucleosomal repeats, a typical feature of apoptosis. No internucleosomal DNA fragmentation was observed in vector-transfected cells. These results suggest that overexpression of ICE related protease mRNA induces a DNA fragmentation pattern characteristic of apoptosis.

EXAMPLE 3
Influence Of Extracellular Potassium On Ice Related Protease Gene And Granule Neurons Postmitotic cerebellar granule neurons are readily maintained in vitro in their fully differentiated state for several weeks under depolarizing conditions (HK, 25 mM K$^+$). When the medium is changed to non-depolarizing conditions (LK, 5 mM K$^+$), the neurons subsequently die and display morphological features of apoptosis including cytoplasmic blebbing and heterochromatic clumping. To investigate whether an ICE related protease is involved in the granule neuronal apoptosis process, RNA derived from neurons switched from HK to LK were probed with labeled ICE related protease cDNA.

3A. Preparation Of Cultured Cerebellar Granule Neurons

Cerebellar granule neurons (PND8) were prepared from 8-day-old Sprague-Dawley rat pups (15–19 g) as previously described in A. M. Marini and S. M. Paul, N-methyl-D-aspartate Receptor-mediated Neuropection In Cerrebellar Granule Cells Requires New RNA and Protein Synthesis, *Proc. Natl. Acad. Sci, USA* 89:6555–59 (1992). Briefly, cells were dissociated from freshly dissected cerebelli by mechanical disruption in the presence of trypsin and DNase and then plated in poly-l-lysine-coated 35 mm culture plates. Cells were seeded at a density of $1.5–1.8×10^6$ cells/ml (2 ml/dish) in basal modified Eagle's medium containing 10% fetal bovine serum and 25 mM KCl. Cytosine arabinoside (10 μM) (Ara-C) was added to the culture medium after 24 h to arrest the growth of non-neuronal cells. D-glucose (100 ul of a 100 mM solution prepared in sterile $H_2O$) was added to the cultures on day 7 and every fourth day thereafter.

3B. Assessment of neuronal viability and detection of DNA fragmentation

Cerebellar granule neurons were prepared as described above and exposed to HK and LK conditions for 8 DIV. Cerebellar granule neurons were maintained in parallel sister cultures in medium under depolarizing conditions (HK, 25 mM K+). One culture of the cerebellar granule neurons was then switched to medium with non-depolarizing conditions (LK, 5 mM K+). At varying time points (for a period of 24 hours), cerebellar granule neurons were cultured and RNA was extracted from the cultured cerebellar granule neurons by using standard procedures. Representative samples were obtained at varying time intervals as follows: HK at 8 hrs and 24 hrs and LK at 1 hr, 4 hrs, 8 hrs and 24 hrs.

Viable granule neurons were quantified after staining with fluorescein diacetate, which is deesterified only by living cells (A. M. Marini and S. M. Paul, N-methyl-D-aspartate Receptor-mediated Neuropection In Cerebellar Granule Cells Requires New RNA and Protein Synthesis, *Proc. Natl. Acad. Sci, USA* 89:6555–59 (1992) and G. Yan, et al., Depolarization Or glutamate Receptor Activation Blocks Apoptotic Cell Death Of Cultured Cerebellar Granule Neurons, *Brain Res.* 656:43–51 (1995)). Briefly, after incubation with fluorescein diacetate (10 μg/ml; Sigma) neurons were examined and photographed under UV light microscopy and the number of neurons per representative low-power field were counted from the photomicrographs. Values are generally expressed as the % of control cultures in each experiment. HK neurons showed normal nuclear morphology whereas those in LK medium demonstrated nuclear condensation typical of apoptotic cells.

Northern Blot analysis of extracted RNA was performed. The Northern Blots utilized for the rat brain RNA were obtained from Clontech (Catalog #7764-1). The various samples (20 μg/lane) were loaded and run on a 1.5% agarose gel using standard conditions. The resulting agarose gels were stained with ethidium bromide and then transferred to nitrocellulose blots. The blots were prehybridized at 42° C. for 2 hrs in buffer containing 50% formamide, 5×SSPE, 10×Denhardt's, 2% SDS, and 100 μg/ml salmon sperm DNA. Hybridization was carried out overnight in the same buffer containing denatured $^{32}$P-labeled cDNAs from the ICE related protease clone and/or human β-actin. The blots were then washed at 50° C. in 2×SSC, 0.1% SDS and exposed to X-ray film at −70° C. with a Cronex lightening plus intensifying screen using double intensifying screen for two days.

ICE related protease transcripts were dramatically induced in cultured granule neurons 4 and 8 hr after switching from HK to LK medium. Low amount of RNA loaded on the gel from 24 hr LK culture resulted from cell death of granule neurons (≧80%) 24 hr at LK medium.

Total RNA (20 ug) was isolated from each condition 8 hr after switching to LK medium. ICE related protease mRNA is induced in granule neurons 8 hr after changing medium from HK to LK, consistent with time course of ICE related protease mRNA induction. However, the induction of ICE related protease mRNA was completely blocked by replenishment with 20 mM KCl 30 min and 90 min after switching from HK to LK medium.

Using Northern analysis as described above, the expression of the Nedd2 gene, a cell death gene which is developmentally-regulated and shown to be expressed in early embryonic brain was also examined (S. Kumar, et al., Induction Of Apoptosis By Mouse Nedd2 Gene Which Encodes A Protein Similar To The Product Of Caenorhabditis Elegans Cell Death Gene Ced-3 And Mammalian IL-1β-converting Enzyme, *Gene & Develop* 8:1613–26 (1994)). The Nedd2 transcript is not detectable in cultured cerebellar granule neurons at PND8 in either HK or LK medium.

Western blot analysis of the HK 24 hr sample and the LK 24 hr sample was also performed. For Western blotting, protein samples (20 μg/lane)from each time point were separated by electrophoresis using standard conditions and then transferred to a nylon membrane. Western blotting was carried out by using the ECL method as described by the manufacturer (Amersham, Ill.). Briefly, blots were incubated in PBS plus 0.1% Tween-20 (PBS-T) containing 5% milk powder for 1 hr followed by several washes with PBS-T in room temperature and then incubated with primary antibody c-2-10 diluted in 1:10,000 for 2–3 hr. After washing with PBS-T, membranes were incubated with HRP-labeled antibody (1:2000 dilution) for 1 hr at room temperature. The blots were subsequently washed several times in PBS-T to remove the secondary antibody. Finally, the membranes were developed with ECL detection system and exposed to X-ray film.

DNA fragmentation characteristic of apoptotic death was induced in cerebellar granular neurons by switching to LK medium. Soluble DNA was isolated using the procedures indicated in Example 1 from both HK and LK cells 24 hr after switching the medium. Soluble DNA isolated from granule neurons switched to LK medium showed characteristic DNA fragmentation.

The induction of apoptosis due to changing cultured cerebellar granule neurons from HK to LK medium is completely blocked by the addition of both cycloheximide and actinomycin D (G. Yan et al., Depolarization Or Glutamate Receptor Activation Blocks Apoptotic Cell Death Of Cultured Cerebellar Granule Neurons, *Brain Res.* 656:43–51 (1994). Moreover, both induction of ICE related protease mRNA and apoptosis of cerebellar granule neurons induced by LK medium can be completely prevented by raising $[K^+]_e$ to 20 mM KCl ≦90 min after exposure to nondepolarizing conditions. This is well coordinated with granule neuron death induced by the KCl deficiency-mediated neurotoxicity shown.

Granule neuron death can only be partially prevented (assessed at 24 hr after switching the medium) by the addition of depolarizing $[K^+]e$ (20 mM KCl) ≧4 hr after being switched to the LK medium. The latter corresponds to a time point near the commitment point for LK-induced apoptosis (Yan et al. personal communication; C. Galli et al., Apoptosis In Cerebellar Granule Cells Is Blocked By High KCl, Forskolin, And IGF-1 Through Distinct Mechanisms Of Action: The Involvement Of Intracellular Calcium And RNA Synthesis, *J. Neurosci.* 12:1172–79 (1995)) and the point when overexpression of the ICE related protease gene has been induced. These findings suggest that suppression of ICE related protease gene expression by raising $[K^+]e$ is associated with cell viability. Moreover, KCl deficiency-mediated granule neuron death is associated with overexpression of the ICE related protease gene, consistent with its induction of apoptosis in transfected mammalian cells.

Monoclonal antibody 2-c-10 against poly(ADP-ribose) polymerase (PARP) (M. Tewari et al., Yama/CPP32β, A Mammalian Homolog Of CED-3 Is A CrmA-inhibitable Protease That Cleaves The Death Substrate Poly-ribose Polymerase, *Cell* 8:801–9 (1995) and Y. A. Lazebnik et al., Cleavage Of Poly(ADP-ribose) Polymerase By A Proteinase With Properties Like ICE, *Nature* 371:346–7 (1995)) was used to examine whether the upregulation of ICE related protease subsequently leads to cleavage of this death substrate. Granule neurons were lysed using lysis buffer from each time point after switching from HK to LK medium. Total proteins were separated by SDS-PAGE. Immunoblots were incubated with monoclonal antibody C-2-10 and visualized with ECL as described above. PARP is cleaved to the 89 kDa fragment 8 and 24 hr after switching from HK to LK medium. A cleavage product (89 kDa fragment) of PARP is clearly present at 8 and 24 hr after changing from HK to LK medium, which is also in good agreement with the time courses of induction of the ICE related protease transcript and manifestation of apoptotic cell death.

Since the cysteine protease, ICE related protease, like the other cysteine proteases, can cleave PARP, it should therefore be designated as a prICE family member. Overexpression of ICE related protease in mammalian cells induces characteristic internucleosomal DNA fragmentation, a typical feature of apoptosis. Unlike ICE, however, ICE related protease is present in the CNS and is enriched in central neurons including pyramidal neurons and granule neurons of the hippocampus and cerebral cortex. Furthermore, non-depolarizing conditions, which are known to trigger the apoptotic machinery of cultured cerebellar granule neurons (G. Yan, et al., Depolarization Or glutamate Receptor Activation Blocks apoptotic Cell Death Of Cultured Cerebellar Granule Neurons, *Brain Res.* 656:43–51 (1994) and S. R. D'Mello, et al., Induction Of Apoptosis In Cerebellar Granule Neurons By Low Potassium: Inhibition By Insulin-like Growth Factor I And cAMP, *Proc. Natl. Acad. Sci. USA* 90:10989–93 (1993), induces overexpression of the ICE related protease gene. Apoptosis can be readily induced in cultured cerebellar granule neurons after switching from HK to LK medium and the latter is associated with the characteristic DNA fragmentation, cleavage of the death substrate, PARP and morphology of apoptosis. Several previous experiments have demonstrated that activity of ICE related protease(s) can be auto-activated (auto-cleaved) in concentration-dependent manner, suggesting that overexpression of ICE related protease could contribute to its autoactivation of its catalytic (protease) activity. Thus, activation of this cell death machinery can occur not only through activation of an ICE related protease(via proteolytic processing of its processor protein) but also by induced expression (increased transcription) of the protease gene itself (presumably leading to increase in the protease protein).

The induction of ICE related protease mRNA in cultured cerebellar granule neurons exposed to non-depolarizing conditions is robust and coincides (precedes) cell death. Moreover, the expression of ICE related protease mRNA occurs following the commitment point for apoptosis and can be prevented by high K+(depolarizing conditions) prior to the commitment point. The fact that ICE related protease can induce apoptosis when transfected in mammalian cells is consistent with its possible role in inducing apoptosis in cerebellar granule neurons. Using the same hybridization conditions, we could not detect the presence of Nedd2 transcripts, (another ICE-like cell death gene which is developmentally-regulated) in cultured cerebellar granule neurons prepared from cultures exposed to LK conditions. In addition, previous studies have shown that ICE or the ICH/Nedd2 family of protease are unable to cleave PARP into a 89 kDa fragment (M. Tewari, et al., Yama/CPP32β, A Mammalian Homolog Of CED-3, Is A CrmA-inhibitable Protease That Cleaves The Death Substrate Poly-ribose Polymerase, *Cell* 8:801–9 (1995); Y.A. Lazebnik, et al., Cleavage of Poly(ADP-ribose) Polymerase By A Proteinase With Properties Like ICE, *Nature* 371:346–47 (1995)) whereas co-transfection of ICE, Tx, Nedd2 and PARP suggest that these proteases generate a 31 kDa fragment of PARP (Y. Gu, et al., Cleavage Of Poly(AP-ribose) Polymerase By Interleukin-1b Converting Enzyme And Its Homologs TX and Nedd-2, *J. Biol. Chem.* 270:18715–18 (1995)). Taken together, these data suggest that Nedd2 does not play a significant role in the cell death of cultured cerebellar granule neurons induced by non-depolarizing culture conditions. However, the data does not exclude involvement of other ICE related protease in the death cascade of cultured cerebellar granule neurons.

The highest sequence homology between ICE related proteases lies in the active site containing the Cys residue required for proteolytic activity. This site was therefore used as a consensus sequence for generating the degenerate oligonucleotide probes for screening of a rat brain cDNA library that led to the cloning of ICE related protease. Consequently, ICE related protease shares a highly conserved active site common to all ICE related proteases, and not surprisingly shows a high degree of identity to CPP32/YAMA/apopain. These observations suggest that ICE related protease may be related to CPP32/YAMA/apopain, although the degree of homology between ICE related protease and CPP32/YAMA/apopain is not high enough to firmly support this conclusion. Furthermore, it is not clear whether CPP32/YAMA/apopain is expressed in rat CNS. The present invention suggests that ICE related protease described herein is a novel ICE related protease whose expression is dramatically upregulated in mammalian neurons which are induced to apoptose in culture.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1177 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 76..906

( x i ) SEQUENCE DESCRIPTION: SEQ ID NO:1:

```
GAATTCGGCT  TGGTAGCGAC  CGGCGCTCAG  CTGGAATTCC  GGGGAGCTTG  GAACGGTACG              6 0

CGAAGAAAAG  TGACC  ATG  GAC  AAC  AAC  GAA  ACC  TCC  GTG  GAT  TCA  AAA  TCC     1 1 1
```

```
                        Met Asp Asn Asn Glu Thr Ser Val Asp Ser Lys Ser
                         1               5                  10

ATT AAT AAT TTT GAA ACA AAG ACT ATC CAT GGA AGC AAG TCG ATG GAC      159
Ile Asn Asn Phe Glu Thr Lys Thr Ile His Gly Ser Lys Ser Met Asp
         15              20              25

TCT GGA ATA TAT CTG GAC AGC AGT TAC AAA ATG GAT TAC CCT GAA ATG      207
Ser Gly Ile Tyr Leu Asp Ser Ser Tyr Lys Met Asp Tyr Pro Glu Met
     30              35              40

GGC TTG TGT ATA ATA ATT AAT AAT AAG AAC TTC CAT AAA AGC ACT GGA      255
Gly Leu Cys Ile Ile Ile Asn Asn Lys Asn Phe His Lys Ser Thr Gly
 45              50              55                          60

ATG TCA GCT CGC AAT GGT ACC GAT GTC GAT GCA GCT AAC CTC AGA GAG      303
Met Ser Ala Arg Asn Gly Thr Asp Val Asp Ala Ala Asn Leu Arg Glu
             65              70              75

ACA TTC ATG GCC CTG AAA TAC GAA GTC AGG AAT AAA AAT GAC CTT ACT      351
Thr Phe Met Ala Leu Lys Tyr Glu Val Arg Asn Lys Asn Asp Leu Thr
             80              85              90

CGT GAA GAA ATT ATG GAA TTG ATG GAT AGT GTT TCT AAG GAA GAT CAC      399
Arg Glu Glu Ile Met Glu Leu Met Asp Ser Val Ser Lys Glu Asp His
         95              100             105

AGC AAA AGG AGC AGT TTT GTG TGT GTG ATT CTA AGT CAT GGA GAT GAA      447
Ser Lys Arg Ser Ser Phe Val Cys Val Ile Leu Ser His Gly Asp Glu
 110             115             120

GGA GTA ATT TTT GGA ACG AAC GGA CCT GTG GAC CTG AAA AAA CTA ACT      495
Gly Val Ile Phe Gly Thr Asn Gly Pro Val Asp Leu Lys Lys Leu Thr
125             130             135                          140

AGT TTC TTC AGA GGC GAC TAC TGC CGG AGT CTG ACT GGA AAG CCG AAA      543
Ser Phe Phe Arg Gly Asp Tyr Cys Arg Ser Leu Thr Gly Lys Pro Lys
             145             150             155

CTC TTC ATC ATT CAG GCC TGC CGA GGT ACA GAG CTG GAC TGC GGT ATT      591
Leu Phe Ile Ile Gln Ala Cys Arg Gly Thr Glu Leu Asp Cys Gly Ile
             160             165             170

GAG ACA GAC AGT GGA ACT GAC GAT GAT ATG GCA TGC CAG AAG ATA CCA      639
Glu Thr Asp Ser Gly Thr Asp Asp Asp Met Ala Cys Gln Lys Ile Pro
             175             180             185

GTG GGG GCC GAC TTC CTG TAT GCT TAC TCT ACC GCA CCC GGT TAC TAT      687
Val Gly Ala Asp Phe Leu Tyr Ala Tyr Ser Thr Ala Pro Gly Tyr Tyr
 190             195             200

TCC TGG AGA AAT TCA AGG GAC GGG TCA TGG TTC ATC CAG TCA CTT TGC      735
Ser Trp Arg Asn Ser Arg Asp Gly Ser Trp Phe Ile Gln Ser Leu Cys
205             210             215                          220

GCC ATG CTG AAA CTG TAC GCG CAC AAG CTG GAA TTC ATG CAC ATC CTC      783
Ala Met Leu Lys Leu Tyr Ala His Lys Leu Glu Phe Met His Ile Leu
             225             230             235

ACT CGT GTT AAC CGG AAG GTG GCC ATG GAA TTT GAG TCC TTC TCC CTG      831
Thr Arg Val Asn Arg Lys Val Ala Met Glu Phe Glu Ser Phe Ser Leu
             240             245             250

GAC GCC ACT TTC CAC GCA AAG AAA CAG ATC CCG TGT ATT GTG TCA ATG      879
Asp Ala Thr Phe His Ala Lys Lys Gln Ile Pro Cys Ile Val Ser Met
             255             260             265

CTC ACA AAA GAA CTG TAC TTT TAT CAC TAAAGGAATG ACTGGGAGTG            926
Leu Thr Lys Glu Leu Tyr Phe Tyr His
             270             275

GGGTAGGGGC ATGTTTCTGT TTTGGTTTTT TTTTGGTTTT TGGTTTGTTT TTTTTTTTT     986

TATTTGAATG CCAAATGAGA AAACTGTCAG GGAGACTTTT TTTTTCCCCT CTCATTTAAA    1046

TCAAATCCGA TGTTCCAGGT CGTCATTGAA CAATACCACT GCCTGCAATG CAGCCACAAT    1106

ACAATACCTC AGCTTTGATA TCAGCCGGAA TTCCGCCGAT ACTGACGGGC TCCAGGAGTC    1166

AAGCCGAATT C                                                        1177
```

( 2 ) INFORMATION FOR SEQ ID NO:2:

( i ) SEQUENCE CHARACTERISTICS:
        ( A ) LENGTH: 277 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Asn  Asn  Glu  Thr  Ser  Val  Asp  Ser  Lys  Ser  Ile  Asn  Asn  Phe
 1                    5                   10                        15
Glu  Thr  Lys  Thr  Ile  His  Gly  Ser  Lys  Ser  Met  Asp  Ser  Gly  Ile  Tyr
               20                   25                        30
Leu  Asp  Ser  Ser  Tyr  Lys  Met  Asp  Tyr  Pro  Glu  Met  Gly  Leu  Cys  Ile
           35                   40                        45
Ile  Ile  Asn  Asn  Lys  Asn  Phe  His  Lys  Ser  Thr  Gly  Met  Ser  Ala  Arg
      50                        55                   60
Asn  Gly  Thr  Asp  Val  Asp  Ala  Ala  Asn  Leu  Arg  Glu  Thr  Phe  Met  Ala
 65                        70                   75                        80
Leu  Lys  Tyr  Glu  Val  Arg  Asn  Lys  Asn  Asp  Leu  Thr  Arg  Glu  Glu  Ile
                85                        90                        95
Met  Glu  Leu  Met  Asp  Ser  Val  Ser  Lys  Glu  Asp  His  Ser  Lys  Arg  Ser
               100                       105                  110
Ser  Phe  Val  Cys  Val  Ile  Leu  Ser  His  Gly  Asp  Glu  Gly  Val  Ile  Phe
          115                       120                  125
Gly  Thr  Asn  Gly  Pro  Val  Asp  Leu  Lys  Lys  Leu  Thr  Ser  Phe  Phe  Arg
     130                       135                  140
Gly  Asp  Tyr  Cys  Arg  Ser  Leu  Thr  Gly  Lys  Pro  Lys  Leu  Phe  Ile  Ile
145                      150                  155                      160
Gln  Ala  Cys  Arg  Gly  Thr  Glu  Leu  Asp  Cys  Gly  Ile  Glu  Thr  Asp  Ser
               165                       170                       175
Gly  Thr  Asp  Asp  Asp  Met  Ala  Cys  Gln  Lys  Ile  Pro  Val  Gly  Ala  Asp
               180                       185                  190
Phe  Leu  Tyr  Ala  Tyr  Ser  Thr  Ala  Pro  Gly  Tyr  Tyr  Ser  Trp  Arg  Asn
          195                       200                  205
Ser  Arg  Asp  Gly  Ser  Trp  Phe  Ile  Gln  Ser  Leu  Cys  Ala  Met  Leu  Lys
     210                       215                  220
Leu  Tyr  Ala  His  Lys  Leu  Glu  Phe  Met  His  Ile  Leu  Thr  Arg  Val  Asn
225                      230                       235                  240
Arg  Lys  Val  Ala  Met  Glu  Phe  Glu  Ser  Phe  Ser  Leu  Asp  Ala  Thr  Phe
               245                       250                       255
His  Ala  Lys  Lys  Gln  Ile  Pro  Cys  Ile  Val  Ser  Met  Leu  Thr  Lys  Glu
               260                       265                       270
Leu  Tyr  Phe  Tyr  His
               275
```

( 2 ) INFORMATION FOR SEQ ID NO:3:

( i ) SEQUENCE CHARACTERISTICS:
        ( A ) LENGTH: 1177 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:3:

-continued

| | | | | |
|---|---|---|---|---|
| GAAUUCGGCU | UGGUAGCGAC | CGGCGCUCAG | CUGGAAUUCC | GGGGAGCUUG | GAACGGUACG | 60 |
| CGAAGAAAAG | UGACCAUGGA | CAACAACGAA | ACCUCCGUGG | AUUCAAAAUC | CAUUAAUAAU | 120 |
| UUUGAAACAA | AGACUAUCCA | UGGAAGCAAG | UCGAUGGACU | CUGGAAUAUA | UCUGGACAGC | 180 |
| AGUUACAAAA | UGGAUUACCC | UGAAUGGGC | UUGUGUAUAA | UAAUUAAUAA | UAAGAACUUC | 240 |
| CAUAAAAGCA | CUGGAAUGUC | AGCUCGCAAU | GGUACCGAUG | UCGAUGCAGC | UAACCUCAGA | 300 |
| GAGACAUUCA | UGGCCCUGAA | AUACGAAGUC | AGGAAUAAAA | AUGACCUUAC | UCGUGAAGAA | 360 |
| AUUAUGGAAU | UGAUGGAUAG | UGUUUCUAAG | GAAGAUCACA | GCAAAAGGAG | CAGUUUUGUG | 420 |
| UGUGUGAUUC | UAAGUCAUGG | AGAUGAAGGA | GUAAUUUUUG | GAACGAACGG | ACCUGUGGAC | 480 |
| CUGAAAAAAC | UAACUAGUUU | CUUCAGAGGC | GACUACUGCC | GGAGUCUGAC | UGGAAAGCCG | 540 |
| AAACUCUUCA | UCAUUCAGGC | CUGCCGAGGU | ACAGAGCUGG | ACUGCGGUAU | UGAGACAGAC | 600 |
| AGUGGAACUG | ACGAUGAUAU | GGCAUGCCAG | AAGAUACCAG | UGGGGGCCGA | CUUCCUGUAU | 660 |
| GCUUACUCUA | CCGCACCCGG | UUACUAUUCC | UGGAGAAAUU | CAAGGGACGG | UCAUGGUUC | 720 |
| AUCCAGUCAC | UUUGCGCCAU | GCUGAAACUG | UACGCGCACA | AGCUGGAAUU | CAUGCACAUC | 780 |
| CUCACUCGUG | UUAACCGGAA | GGUGGCCAUG | GAAUUUGAGU | CCUUCUCCCU | GGACGCCACU | 840 |
| UUCCACGCAA | AGAAACAGAU | CCCGUGUAUU | GUGUCAAUGC | UCACAAAAGA | ACUGUACUUU | 900 |
| UAUCACUAAA | GGAAUGACUG | GGAGUGGGGU | AGGGGCAUGU | UUCUGUUUUG | GUUUUUUUU | 960 |
| GGUUUUUGGU | UUGUUUUUU | UUUUUUUAUU | UGAAUGCCAA | AUGAGAAAAC | UGUCAGGGAG | 1020 |
| ACUUUUUUUU | UCCCCUCUCA | UUUAAAUCAA | AUCCGAUGUU | CCAGGUCGUC | AUUGAACAAU | 1080 |
| ACCACUGCCU | GCAAUGCAGC | CACAAUACAA | UACCUCAGCU | UUGAUAUCAG | CCGGAAUUCC | 1140 |
| GCCGAUACUG | ACGGGCUCCA | GGAGUCAAGC | CGAAUUC | | | 1177 |

What is claimed is:

1. An isolated polypeptide which comprises the amino acid sequence

Met Asp Asn Asn Glu Thr Ser Val
1               5

Asp Ser Lys Ser Ile Asn Asn Phe
             10                    15

Glu Thr Lys Thr Ile His Gly Ser
              20

Lys Ser Met Asp Ser Gly Ile Tyr
         25                    30

Leu Asp Ser Ser Tyr Lys Met Asp
         35                    40

Tyr Pro Glu Met Gly Leu Cys Ile
                             45

Ile Ile Asn Asn Lys Asn Phe His
     50                    55

Lys Ser Thr Gly Met Ser Ala Arg
                        60

Asn Gly Thr Asp Val Asp Ala Ala
65                    70

Asn Leu Arg Glu Thr Phe Met Ala
                  75                    80

Leu Lys Tyr Glu Val Arg Asn Lys
                     85

-continued

Asn Asp Leu Thr Arg Glu Glu Ile
     90                    95

Met Glu Leu Met Asp Ser Val Ser
              100

Lys Glu Asp His Ser Lys Arg Ser
105                    110

Ser Phe Val Cys Val Ile Leu Ser
         115                    120

His Gly Asp Glu Gly Val Ile Phe
                        125

Gly Thr Asn Gly Pro Val Asp Leu
     130                    135

Lys Lys Leu Thr Ser Phe Phe Arg
                   140

Gly Asp Tyr Cys Arg Ser Leu Thr
145                    150

Gly Lys Pro Lys Leu Phe Ile Ile
              155                    160

Gln Ala Cys Arg Gly Thr Glu Leu
                   165

Asp Cys Gly Ile Glu Thr Asp Ser
         170                    175

Gly Thr Asp Asp Asp Met Ala Cys
              180

Gln Lys Ile Pro Val Gly Ala Asp
     185                    190

```
Phe  Leu  Tyr  Ala  Tyr  Ser  Thr  Ala
          195                      200
                    Pro  Gly  Tyr  Tyr  Ser  Trp  Arg  Asn
                                   205
Ser  Arg  Asp  Gly  Ser  Trp  Phe  Ile
     210                      215
                    Gln  Ser  Leu  Cys  Ala  Met  Leu  Lys
                              220
Leu  Tyr  Ala  His  Lys  Leu  Glu  Phe
225                      230
                    Met  His  Ile  Leu  Thr  Arg  Val  Asn
                              235                      240
Arg  Lys  Val  Ala  Met  Glu  Phe  Glu
               245
                    Ser  Phe  Ser  Leu  Asp  Ala  Thr  Phe
                         250                      255
His  Ala  Lys  Lys  Gln  Ile  Pro  Cys
               260

Ile  Val  Ser  Met  Leu  Thr  Lys  Glu
          265                      270
Leu  Tyr  Phe  Tyr  His
          275
``` which is designated as SEQ ID NO:2.

2. A method to identify compounds that inhibit the apoptotic process, comprising the steps of:

(a) isolating an ICE related protease, comprising the polypeptide of SEQ ID No:2;

(b) exposing said ICE related protease to a potential inhibitor to this protease;

(c) introducing a suitable substrate; and (d) quantifying the amount of cleavage of the substrate, relative to a control in which no potential inhibitor has been added.

* * * * *